United States Patent [19]

Tahara et al.

[11] 4,380,668
[45] * Apr. 19, 1983

[54] DECAPRENYLAMINE DERIVATIVES

[75] Inventors: Yoshiyuki Tahara, Ohi; Hiroyasu Koyama, Ageo; Yasuhiro Komatsu, Niiza; Reiko Kubota, Tokyo; Toshihiro Takahashi, Ohi, all of Japan

[73] Assignee: Nisshin Flour Milling Co., Ltd., Tokyo, Japan

[*] Notice: The portion of the term of this patent subsequent to Mar. 30, 1999, has been disclaimed.

[21] Appl. No.: 208,324

[22] Filed: Nov. 19, 1980

[51] Int. Cl.³ .................. C07C 87/28; A61K 31/13; C07D 213/06; A61K 31/44

[52] U.S. Cl. .................. 564/391; 546/304; 546/329; 564/305; 564/374; 424/263; 424/330

[58] Field of Search .......... 546/304, 329, 391, 374, 546/305

[56] References Cited

U.S. PATENT DOCUMENTS

| | | | |
|---|---|---|---|
| 3,350,451 | 10/1967 | Smutny | 564/374 X |
| 3,444,202 | 5/1969 | Chung et al. | 564/391 X |
| 4,139,560 | 2/1979 | Reinehr et al. | 546/329 X |
| 4,322,555 | 3/1982 | Tahara et al. | 564/305 |

Primary Examiner—Joseph Paul Brust
Attorney, Agent, or Firm—Abelman, Frayne & Rezac

[57] ABSTRACT

This invention relates to new decaprenylamines and the acid addition salts thereof, which are useful for controlling virus infection of vertebrate animals.

3 Claims, No Drawings

DECAPRENYLAMINE DERIVATIVES

There are known heretofore various substances, which have been decided to have preventive or alleviative effects on diseases caused by virus whose host is a vertebrate animal, or which have been recognized to be capable of alleviating symptoms of the diseases by significantly enhancing antibody activity in the animal. Antivirotics reported so far include interferon, substances capable of inducing interferon, i.e. inducers (interferon inducers), amantadine hydrochloride or synthetic substances, such as methysazone, which directly exert inhibitory effect on the virus propagation. Interferon is glycoprotein having antiviral and antitumor activity, said glycoprotein being produced in situ by cells of a vertebrate animal when the cells are infected with virus, and has been suggested for the therapy of infectious viral disease and also for the therapy of cancer. Known inducers, which induce interferon in vertebrate animals by a process other than the virus infection, include natural high molecular substances such as double chain ribonucleic acid of bacteriophage of a certain species, or synthetic high molecular substances such as double chain ribonucleic acid, typical of which is polyinosinic acid-polycytidylic acid, or low molecular inducers such as tyrolone.

In the production of interferon, however, there is involved a problem how to carry out the purification thereof, and in fact no economical process for the production thereof has not been established yet. On the other hand, conventional interferon inducers have not been put to practical use mainly because of toxicity thereof. Synthetic antiviral agents which directly exert inhibitory effect on the virus propagation, which are commercially available at present, have a rather narrow range of virus-infected diseases which are curable by administration of said agent, and thus the advent of novel synthetic antiviral agents is earnestly desired. Taking such circumstances into consideration, the present inventors extensively conducted studies in finding compounds capable of producing interferon of high potency and, moreover, having antiviral activity on the biological level, and as the result they have eventually found that compounds represented by the following general formula (I) and acid addition salts thereof show excellent interferon inducing ability and, at the same time, demonstrate excellent antiviral activity even in the biological test.

Thus, the present invention is to provide a new class of a decaprenylamine derivative represented by the following general formula

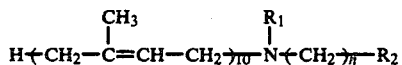

wherein n represents an integer of 0–2, $R_1$ represents hydrogen atom, a lower alkyl group or decaprenyl group, and $R_2$ represents a phenyl group or a pyridyl group, and acid addition salts thereof.

For the production of decaprenylamine represented by the above-mentioned general formula (I) and acid addition salts thereof, there may be adopted a process in which the known procedures for the amine synthesis are applied to the starting decaprenol represented by the formula

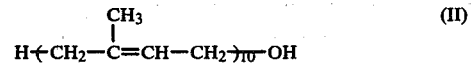

to produce a desired amine derivative.

Further, the amine derivative thus obtained may be converted into a corresponding salt in the usual way. More specifically, a desired amine can be produced according to a process which comprises converting a suitable decaprenyl alcohol of the aforesaid general formula (II) into a corresponding halide or sulfonic acid ester, followed by reaction with an appropriate primary or secondary amino compound corresponding to the desired final product in the presence or absence of a base. Alternatively, the desired amine can be produced by the oxidation of a decaprenol to a corresponding aldehyde, which is then condensed with an appropriate primary amino compound, with splitting off of water, to form a corresponding imino compound which in turn is reduced with a suitable reducing agent (e.g. sodium borohydride). An acid addition salt of the amine derivative thus obtained can be obtained by mixing said amine in an appropriate solvent with a desired acid to form a salt and crystallizing the salt out of the solution by evaporation or other means to recover the same. The acid addition salts suitable for use as medicines include, for example, those with hydrochloric acid, acetic acid, citric acid, fumaric acid and the like.

The compounds represented by the general formula (I) and acid addition salts thereof are illustrated below with reference to preparative example.

PREPARATIVE EXAMPLE 1

N-benzyl-didecaprenylamine hydrochloride

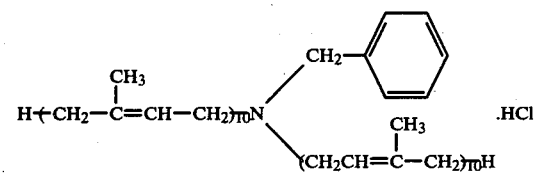

To a solution of benzylamine (10 g.) in ethanol (100 ml) a solution of decaprenyl bromide (20 g.) in benzene (40 ml) was added dropwise at room temperature for 1 hour with stirring, which was continued for further 2 hours. Thereafter, the resulted mixture was heated at reflux for 2 hours with stirring. The resulting reaction mixture after cooling was added with a 2 N sodium hydroxide aqueous solution (100 ml) and then extracted with isopropylether. The liquid extract obtained was washed with water and saturated saline, dried over anhydrous sodium sulfate and then concentrated under reduced pressure. The residue (21.4 g.) was purified by column chromatography using silica gel (200 g.). Elution was carried out with a mixture of isopropylether and benzene. The initially eluted fraction (7.0 g.) was dissolved in ethyl acetate, added with ether containing HCl to weakly acidic and then cooled. The crystallized mass was separated by filtration to recover N-benzyl-didecaprenylamine hydrochloride (4.9 g.), m.p. 52°–54° C. Elementary analysis as $C_{107}H_{169}N\cdot HCl$ showed the following:

| | C % | H % | N % |
|---|---|---|---|
| Calcd.: | 85.34 | 11.38 | 0.93 |
| Found: | 85.08 | 11.23 | 0.94 |

PREPARATIVE EXAMPLE 2

N-benzyl-decaprenylamine hydrochloride

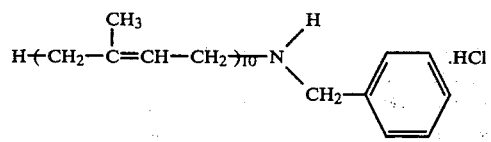

The lastly eluted fraction (7.3 g.) obtained in Preparative Example 1 was dissolved in acetone and then added with ether containing HCl. The mixture was worked up in the same manner as in Example 1, thereby to obtain N-benzyl-decaprenylamine hydrochloride (5.8 g.), m.p. 105°–107° C. Elementary analysis as $C_{57}H_{89}N.HCl$ showed the following:

| | C % | H % | N % |
|---|---|---|---|
| Calcd.: | 83.00 | 11.00 | 1.70 |
| Found: | 82.82 | 10.87 | 1.65 |

PREPARATIVE EXAMPLES 3 TO 9

The same procedures as in Example 1 were carried out for the reaction of decaprenyl bromide with a primary or secondary amino compound thereby to produce the below-indicated compounds, the structural formula, molecular formula, melting point and elementary analysis of which also are listed in Table 1.

TABLE 1

$$H\text{-}(CH_2\text{-}\underset{\underset{CH_3}{|}}{C}=CH\text{-}CH_2)_{\overline{10}}\text{-}\underset{\underset{R_1}{|}}{N}\text{-}(CH_2)_{\overline{n}}\text{-}R_2$$

| Prep. Examp. No. | Structure R₁ | R₂ | n | Molecular formula | m.p.(°C.) or refractive index | Calculated (%) C | H | N | Found (%) C | H | N |
|---|---|---|---|---|---|---|---|---|---|---|---|
| 3 | H | phenyl | 0 | $C_{56}H_{87}N$ | 41–42 | 86.87 | 11.32 | 1.81 | 87.12 | 11.43 | 1.77 |
| 4 | H | pyridyl | 0 | $C_{55}H_{86}N_2$ | 55–56 | 85.21 | 11.18 | 3.61 | 85.03 | 11.37 | 3.51 |
| 5 | H | phenyl | 2 | $C_{58}H_{91}N.HCl$ | 103–105 | 83.05 | 11.05 | 1.67 | 83.15 | 11.18 | 1.61 |
| 6 | $CH_3$ | phenyl | 0 | $C_{57}H_{89}N$ | 37–38 | 86.84 | 11.38 | 1.78 | 86.94 | 11.38 | 1.75 |
| 7 | $CH_3$ | phenyl | 1 | $C_{58}H_{91}N.HCl.H_2O$ | 87–89 | 81.30 | 11.06 | 1.64 | 81.67 | 10.86 | 1.63 |
| 8 | $\text{-}(CH_2CH=\underset{\underset{CH_3}{|}}{C}\text{-}CH_2)_{\overline{10}}H$ | phenyl | 0 | $C_{106}H_{167}N$ | $n_D^{25}=1.5213$ | 87.47 | 11.56 | 0.96 | 87.58 | 11.60 | 0.90 |
| 9 | $\text{-}(CH_2CH=\underset{\underset{CH_3}{|}}{C}\text{-}CH_2)_{\overline{10}}H$ | phenyl | 2 | $C_{108}H_{171}N.HCl.2H_2O$ | 40–43 | 83.36 | 11.40 | 0.90 | 83.01 | 11.18 | 0.82 |

PREPARATIVE EXAMPLES 10 TO 13

To a solution of 3-aminomethylpyridine (25 g.) in ethanol (100 ml) a solution of decaprenyl bromide (30 g.) in chloroform was added dropwise at room temperature for 1 hour with stirring, which was continued for further 3 hours. The resulting reaction mixture after cooling was added with a 2 N sodium hydroxide aqueous solution (100 ml) and extracted with isopropylether. The liquid extract obtained was washed with water and saturated saline, dried over anhydrous sodium sulfate and then concentrated under reduced pressure. The residue (21 g.) was purified by column chromatography using silica gel (200 g.). Elution was carried out with a mixture of 20% ethylacetate 80% hexane. 3-Didecaprenylaminomethylpyridine (Ca. 1.38 g.) was obtained as an oily substance.

The above-said column was further eluted with a mixture of 20% ethanol/80% ethylacetate. The fraction (8.6 g.) was recrystallized from acetone to recover crystalline 3-decaprenylaminomethylpyridine (7.8 g.).

Following the substantially same procedures as mentioned above, 2-(2-decaprenylamino)-ethylpyridine, 2-(2-didecaprenylamino)-ethylpyridine and 3-(N-decaprenyl-N-methylamino)-methylpyridine were obtained.

The physicochemical properties of these compounds are indicated in Table 2.

TABLE 2

$$H{+}CH_2{-}\underset{CH_3}{\underset{|}{C}}{=}CH{-}CH_2{\xrightarrow{}}_{10}\underset{R_1}{\underset{|}{N}}{+}CH_2{\xrightarrow{}}_{n}{-}R_2$$

| Prep. Examp. No. | Structure R₁ | Structure R₂ | n | Molecular formula | m.p.(°C.) or refractive index | Calculated (%) C | Calculated (%) H | Calculated (%) N | Found (%) C | Found (%) H | Found (%) N |
|---|---|---|---|---|---|---|---|---|---|---|---|
| 10-1 | $+CH_2{-}CH{=}\underset{CH_3}{\underset{|}{C}}{-}CH_2{\xrightarrow{}}_{10}H$ | (pyridyl-N) | 1 | $C_{106}H_{168}N_2$ | $n_D^{25.5} = 1.5173$ | 86.58 | 11.51 | 1.91 | 86.46 | 11.60 | 1.86 |
| 10-2 | H | (pyridyl-N) | 1 | $C_{56}H_{88}N_2$ | 28.1–29.2 | 85.21 | 11.24 | 3.55 | 85.04 | 11.34 | 3.33 |
| 11 | H | (pyridyl-N) | 2 | $C_{57}H_{90}N_2 \cdot \tfrac{1}{2}H_2O$ | 28.2–28.6 | 84.28 | 11.29 | 3.45 | 84.52 | 11.33 | 3.29 |
| 12 | $+CH_2{-}CH{=}\underset{CH_3}{\underset{|}{C}}{-}CH_2{\xrightarrow{}}_{10}H$ | (pyridyl-N) | 2 | $C_{107}H_{170}N_2$ | $n_D^{25.5} = 1.5162$ | 86.57 | 11.54 | 1.89 | 86.52 | 11.66 | 1.83 |
| 13 | $CH_3$ | (pyridyl-N) | 1 | $C_{57}H_{90}N_2$ | $n_D^{25.5} = 1.5161$ | 85.21 | 11.29 | 3.49 | 85.11 | 11.37 | 3.30 |

PREPARATIVE EXAMPLE 14

To a solution of N,N-dimethylbenzylamine (10 g.) in ethanol (100 ml), decaprenyl bromide (20 g.) was added dropwise at room temperature for 30 minutes. Stirring is continued for 1.5 hours at room temperature. The resulting reaction mixture is extracted with isopropylether, and the extracted phase was washed with water, dried over anhydrous sodium sulfate and concentrated under reduced pressure. The residue (22.0 g.) obtained was purified by column chromatography on a silica gel. Then, through the column the mixtures of ethylacetate/chloroform with a concentration gradient of 1 to 10% ethylacetate. The eluted fraction (18.6 g.) was dissolved in acetone and the resulting solution was allowed to stand overnight in a refrigerator to recover crystalline N-benzyl-decaprenylammonium bromide (15.8 g.) m.p. 51.2°–53.1° C.

Physiological effects of the compounds of the present invention are illustrated below in detail.

(1) INTERFERON INDUCING ACTIVITY TEST

Each test compound suspended in water with a surfactant was intraperitoneally administered to each group consisting of 5 ICR female mice weighing about 25 g. Twenty hours after administration, blood was collected from the mice and serum was separated therefrom to obtain a serum interferon. The following steps were taken in order to determine potency of the serum interferon thus induced. L-929 cells derived from mice and incubated previously in a monolayer was brought into contact with the test serum solution diluted 10 times, incubated overnight at 37° C. in an incubator placed in carbon dioxide atmosphere and the dilute test serum solution was removed therefrom. Thereafter, the cells were inoculated with vesicular stomatitis virus and placed on a tissue culture medium containing 1% agar. After incubation at 37° C. for 24 hours, the cells were dyed with neutral red solution diluted to an appropriate concentration to count the number of plaques formed thereon and thereby to calculate the plaque inhibition rate in each of the test groups against a group to which no test compound had been administered. The plaque inhibition rate of each test compound is shown in Table 3.

(2) EFFECT ON MICE INFECTED WITH VACCINIA VIRUS

Groups, each consisting of 10 ICR female mice, were intravenously injected vaccinia virus (DIE strain) from the vein of tail. On the 8th day after the inoculation, the number of lesions in form of small pocks on the tail surface was counted after dyeing the tail with ethanol solution containing 1% fluorescein and 0.5% methylene blue. In this test, each test compound was administered intraperitoneally to the mice on the day just before inoculation of the virus, whereby antivirus activity of the test compound was evaluated in terms of inhibition of tail lesions as calculated in each test group against a group to which no test compound had been administered.

The rate of tail lesion inhibition of each test compound is shown in Table 3.

(3) EFFECT ON MICE INFECTED WITH INFLUENZA VIRUS

Groups, each consisting of 10 ICR female mice weighing about 25 g. were challenged by inhalation of neblyzed influenza virus A/PR-8. A solution of each test compound in an aqueous solution containing a surfactant was intraperitoneally administered to the mice 24 hours and 3 hours before the virus infection, and 5 times every other day from the second day after the infection. The mice that survived 21 days after the challenge were regarded as survivors, and survival rate was obtained according to the following equation.

$$\frac{\text{Number of survivors}}{\text{Number of mice treated}} \times 100 = \text{survival rate}$$

TABLE 3

| Test compound | Dose (i.p.) mg/kg | Inhibition of tail lesion (Prevention from vaccinia infection) % | Survival rate (Prevention from influenza injection) % | Plaque inhibition (Serum interferon) % |
|---|---|---|---|---|
| N—methyl-N—phenyl-decaprenylamine | 50 | 29.3 | 50 | 3.8 |
| N—benzyl-decaprenylamine hydrochloride | 50 | 73.2 | 50 | 98.6 |
| N—methyl-N—benzyl-decaprenylamine hydrochloride | 50 | 45.3 | 70 | 24.2 |
| N—phenethyl-decaprenylamine hydrochloride | 50 | 51.6 | 80 | 20.4 |
| 3-didecaprenyl-aminomethylpyridine | 50 | 6.4 | — | — |
| 3-decaprenylamino-methylpyridine | 50 | 47.4 | 70 | — |
| 2-(2-decaprenylamino)ethylpyridine | 50 | 81.1 | 90 | — |
| 2-(2-didecaprenylamino)-ethylpyridine | 50 | 34.5 | — | — |
| 3-(N—decaprenyl-N—methylamino)methylpyridine | 50 | 47.9 | 10 | — |
| Benzyl-decaprenyl-dimethylammonium bromide | 50 | 22.8 | — | — |
| Amantadine hydrochloride (Control) | 50 | — | 40 | — |

(4) TOXICITY

In order to investigate acute toxicity of the compounds of the present invention, 50% lethal dose of each compound was obtained by using ddY male mice weighing 20–25 g. From the results shown in Table 4, it is understood that the compounds had high safety margin by intraperitoneal administration.

TABLE 4

| | 50% Lethal dose (mg/kg) | |
|---|---|---|
| Test compound | Intravenously administered | Intraperitoneally administered |
| N—methyl-N—phenyl-decaprenylamine | 180 | >500 |
| N—benzyl-decaprenylamine hydrochloride | 220 | 315 |
| N—methyl-N—benzyl-decaprenylamine hydrochloride | 377 | >500 |
| N—phenethyl-decaprenylamine hydrochloride | 110 | >500 |
| 3-decaprenylamino-methylpyridine | — | >500 |
| 2-(2-decaprenylamino)-ethylpyridine | — | >500 |

As is clear from the foregoing test results, the active ingredients of the present invention have interferon inducing activity in vivo and are low in toxicity with showing excellent antiviral activity. In the light of the fact that the strict correlation of interferon activity with the individual antivirus activities is not always observed for the present ingredients, there is considered also a possibility that the antivirus activities of said ingredients at biological level are concerned not only in interferon but also in other defensive mechanism of host. Accordingly, when the active ingredients of the present invention are used for treatment of virus-infected diseases, they are administered to patients by such techniques involving oral, inhalant, or the like administration as well as subcutaneous, intramascular and intravenous injection. According to the condition of patient such as age, symptom and route by which the ingredient is administered, the active ingredient of the present invention is used in a dose of 0.5–20 mg/kg, preferably 3–5 mg/kg several times (2–4 times) per day.

The active ingredients of the present invention can be formulated into compositions for medication, for example, tablets, capsules, granules, powder, liquid preparation for oral use, eye lotions, suppositories, ointments, injections and the like.

When the present active ingredients are orally administered, they may be formulated into tablets, capsules, granules or powder. These solid preparations for oral use may contain commonly used excipients, for example, silicic anhydride, metasilicic acid, magnesium alginate, synthetic aluminum silicate, lactose, cane sugar, corn starch, microcrystalline cellulose, hydroxypropylated starch or glycine, and the like; binders, for example, gum arabic, gelatin, tragacanth, hydroxypropyl cellulose or polyvinylpyrrolidone; lubricants, for example, magnesium stearate, talc or silica; disintegrating agents, for example, potato starch and carboxymethyl cellulose; or wetting agents, for example, polyethylene glycol, sorbitan monooleate, hydrogenated castor oil, sodium laurylsulfate. In preparing soft capsules, in particular, the present active ingredients may be formulated by dissolving or suspending them in commonly used oily substrates such as sesame oil, peanut oil, germ oil, fractionated coconut oil such as Miglyol ®, or the like. Tablet or granule preparations may be coated according to the usual method.

Liquid preparation for oral use may be in the form of aqueous or oily emulsion or syrup, or alternatively in the form of dry product which can be re-dissolved before use by means of a suitable vehicle. To these liquid preparations, there may be added commonly used additives, for example, emulsifying aids such as sorbitol syrup, methyl cellulose, gelatin, hydroxyethyl cellulose and the like; or emulsifiers, for example, lecithin, sorbitan monooleate, hydrogenated castor oil, non-aqueous vehicles, for example, fractionated coconut oil, almond oil, peanut oil and the like; or antiseptics, for example, methyl p-hydroxybenzoate, propyl p-hydroxybenzoate or sorbic acid. Further, these preparations for oral use may contain, if necessary, preservatives, stabilizers and the like additives.

In case where the present active ingredients are administered in the form of non-oral suppository, they may be formulated according to the ordinary method using oleophilic substrates such as cacao oil or Witepsol ®, or may be used in the form of rectum capsule obtained by wrapping a mixture of polyethylene glycol, seame oil, germ oil, fractionated coconut oil and the like in a gelatin sheet. The rectum capsule may be coated, if necessary, with waxy materials.

When the present active ingredients are used in the form of injection, they may be formulated into preparations of oil solution, emulsified solution or aqueous solution, and these solutions may contain commonly used emulsifiers, stabilizers or the like additives.

According to the method of administration, the above-mentioned compositions can contain the present active ingredients in an amount of at least 1%, preferably 5 to 50%.

The procedure of formulating the present active ingredients into various preparations is illustrated below with reference to Pharmaceutical Examples.

PHARMACEUTICAL EXAMPLE 1

Hard capsule preparations for oral use

A mixture of 25 g. of N-benzyl-decaprenylamine hydrochloride and 7.5 g. of polyoxyethylene castor oil in acetone was mixed with 25 g. of silicic anhydride. After evaporation of the acetone, the mixture was mixed further with 5 g. of calcium carboxymethylcellulose, 5 g. of corn starch, 7.5 g of hydroxypropylcellulose and 20 g. of microcrystalline cellulose, and 30 ml of water was added thereto and kneaded to give a granular mass. The mass was pelletized by means of a pelletizer (ECK pelletter of Fuji Paudal Co., Japan) equipped with No. 24 mesh (B.S.) screen to obtain granules. The granules were dried to less than 5% moisture content and screened with No. 16 mesh (B.S.) screen. The screened granules were capsuled by means of a capsule filling machine so as to be contained in an amount of 190 mg per capsule.

PHARMACEUTICAL EXAMPLE 2

Soft capsule preparations for oral use

A homogeneous solution was prepared by mixing 50 g. of N-methyl-N-benzyl-decaprenylamine hydrochloride with 130 g. of polyethylene glycol (Macrogol 400). Separately, a gelatin solution was prepared which contained 93 g. of gelatin, 19 g. of glycerine, 10 g. of D-sorbitol, 0.4 g of ethyl p-hydroxybenzoate, 0.2 g. of propyl p-hydroxybenzoate and 0.4 g. of titanium oxide and which was used as a capsule film forming agent. The previously obtained solution, together with the capsule film forming agent, was treated with a manual type flat punching machine to obtaine capsules each having the contents of 180 mg.

PHARMACEUTICAL EXAMPLE 3

Injections

A mixture of 5 g. of N-methyl-N-phenyl-decaprenylamine hydrochloride, an appropriate amount of peanut oil and 1 g. of benzyl alcohol was made a total volume of 100 cc by addition of peanut oil. The solution was portionwise poured in an amount of 1 cc under asepsis operation into an ampule which was then sealed.

PHARMACEUTICAL EXAMPLE 4

Injections

A mixture of 1.0 g of N-phenethyl-decaprenylamine hydrochloride, 5.0 g. of Nikkol HCO 60 (a tradename) (hydrogenated castor oil polyoxyethylene-60 molsether), 20 g. of propylene glycol, 10 g. of glycerol and 5.0 g. of ethyl alcohol was mixed with 100 ml of distilled water and stirred. Under asepsis operation, the solution was portionwise poured in an amount of 1.14 ml into an ampule which was then sealed.

What we claim is:

1. 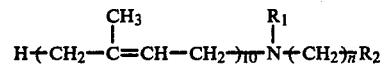

$$H \!-\!\!\left(CH_2-\underset{\underset{CH_3}{|}}{C}=CH-CH_2\right)_{\!\!10}\!\!-\underset{\underset{R_1}{|}}{N}\!\!\left(CH_2\right)_{\!\!n}\!\!R_2$$

wherein n represents an integer of 0–2, $R_1$ represents hydrogen atom, a lower alkyl group or decaprenyl group, and $R_2$ represents the phenyl group, and pharmaceutically acceptable acid addition salts thereof.

2. N-benzyl-decaprenylamine hydrochloride.

3. N-benzyl-didecaprenylamine hydrochloride.

* * * * *